(12) United States Patent
White

(10) Patent No.: US 6,604,943 B2
(45) Date of Patent: Aug. 12, 2003

(54) ORTHODONTIC APPLIANCE

(76) Inventor: Velton C. White, 590 Kearney Rd., Burlington, WI (US) 53105

( * ) Notice: Subject to any disclaimer, the term of this patent is extended or adjusted under 35 U.S.C. 154(b) by 0 days.

(21) Appl. No.: 10/011,574

(22) Filed: Dec. 3, 2001

(65) Prior Publication Data

US 2003/0013062 A1 Jan. 16, 2003

Related U.S. Application Data

(60) Provisional application No. 60/305,682, filed on Jul. 16, 2001.

(51) Int. Cl.[7] .................................................. A61K 7/00
(52) U.S. Cl. ............................................. 433/21; 433/7
(58) Field of Search .............................. 433/6, 7, 18, 21

(56) References Cited

U.S. PATENT DOCUMENTS

| | | |
|---|---|---|
| 360,695 A | 4/1887 | Holmes |
| 3,219,033 A | 11/1965 | Wallshein |
| 3,529,353 A | 9/1970 | Schiaroli |
| 3,827,146 A | 8/1974 | Wallshein |
| 4,026,023 A | 5/1977 | Fisher |
| 4,609,349 A * | 9/1986 | Cain ............................. 433/7 |
| D311,579 S | 10/1990 | Collins, Jr. |
| 5,096,416 A * | 3/1992 | Hulsink ........................ 433/6 |
| 5,310,340 A * | 5/1994 | Zedda ........................... 433/9 |
| 5,580,243 A | 12/1996 | Bloore |
| 5,984,675 A | 11/1999 | White |
| 6,435,871 B1 * | 8/2002 | Inman ........................... 433/7 |

* cited by examiner

Primary Examiner—Cary E. O'Connor
(74) Attorney, Agent, or Firm—Dorr, Carson, Sloan & Birney, P.C.

(57) ABSTRACT

A method and apparatus for orthodontic treatment employs a cast mass-type appliance with a labial bow and combinations of labial and lingual springs to produce multiple coupled forces on selected teeth. The lingual spring has a stem embedded in the appliance and a plurality of pairs of activation loops at its active, tooth-contacting end, which extend laterally outward from the longitudinal axis of the stem. The labial spring has a pair of lateral wings for attachment to a labial bow, and one or more rabbit ears extending selectively either occlusally or gingivally along the labial surface of the tooth.

26 Claims, 4 Drawing Sheets

Fig. 2(a)   Fig. 2(b)

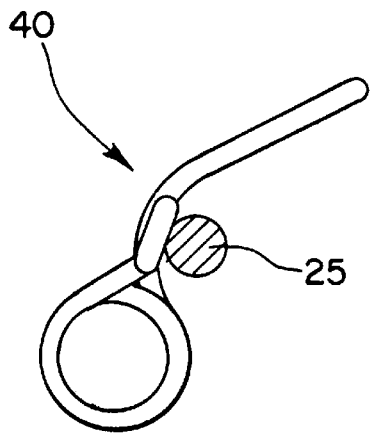
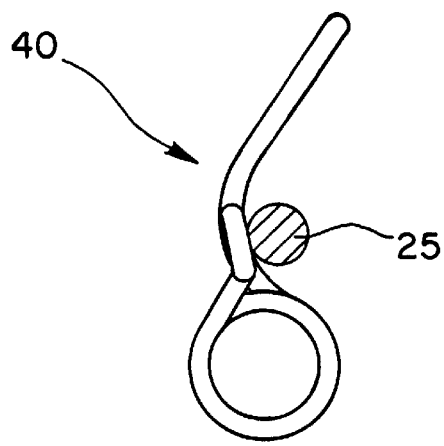
*Fig. 5(a)*    *Fig. 5(b)*
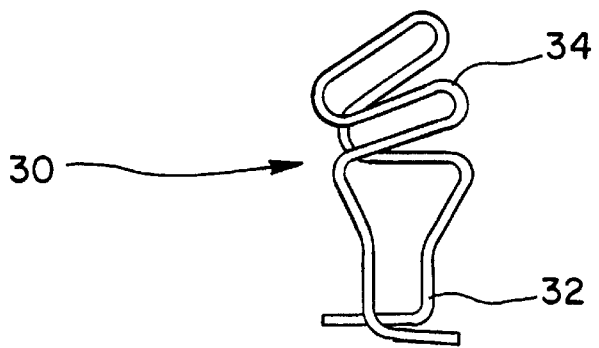
*Fig. 6*

ORTHODONTIC APPLIANCE

RELATED APPLICATION

The present application is based on, and claims priority to the Applicant's U.S. Provisional Patent Application Serial No. 60/305,682, entitled "Orthodontic Appliance," filed on Jul. 16, 2001.

BACKGROUND OF THE INVENTION

1. Field of the Invention

The present invention relates generally to the field of devices and methods for orthodontic treatment, as well as devices useful for maintaining the corrected positions of a patient's teeth after treatment, and more particularly to an improved system of springs useful for returning teeth to desired, treated positions in cases where the corrected orthodontic results have relapsed after treatment.

2. Statement of the Problem

In the field of orthodontics, particularly the area involving the commercial fabrication of orthodontic appliances by orthodontic support laboratories, it is a long-established and well-known practice to conform polymerizing materials into shapes that passively conform to a patient's teeth, gums or palate. Such "cast mass"-type appliances are typically formed from materials such as a dimethacrylate paste activated by a benzoyl peroxide-amine, a self polymerizing methyl methacrylate composition or light curable compositions such as a dimethycrylate paste activated by a camphor quinine, or other heat-softening thermoplastic urethane resins, all of which demonstrate rigid mechanical properties once cast and cured. FIG. 1 is a top perspective view of an example of such an appliance.

It is also common practice for orthodontic laboratories to embed various types of active or passive metallic devices into such cast mass-type appliances during the casting and subsequent curing process. The metallic devices are anticipatorily pre-positioned within the cast mass by a laboratory technician to contact a patient's teeth in desirable ways once the appliance is placed in the patient's mouth. The metallic devices act to urge the teeth to move in desirable ways, including repositioning the teeth into desired or corrected positions and orientations as part of an orthodontist's overall treatment plan.

Such active appliances, when adapted to the upper teeth normally span the top of the patient's mouth in contact with the palate and extend into close proximity to the lingual gingival margins of some or all of a patient's upper teeth. When such an appliance is being fabricated for application to the lower arch, the configuration of the cast mass is significantly relieved compared to the upper configuration. This is to provide clearance for the tongue, and therefore, lower versions of this type of appliance are generally trimmed and contoured to the lateral and anterior aspects of the lingual of the lower dental arch.

The metallic devices that are typically embedded in such an orthodontic appliance are elastically loaded or stated differently, they are capable of storing energy. The metallic devices are deflected by the mal-occluded teeth or in a sense loaded as the appliance is positioned and fully seated in the mouth. The corrective force that directs the teeth into desirable positions is the dissipation, over time, of the energy stored in such deflected metallic devices.

Treatment using such cast mass-type appliances inherently involves the primary corrective forces being generated from the lingual side of the teeth, and therefore such forces are outwardly directed. Such forces are typically simple, single-vector forces that are intended to tip the crown of inwardly canted teeth outward.

Inwardly-acting forces directed to the outside (i.e. the labial and buccal surfaces of the teeth) can also be applied by this type of appliance. To accomplish this, orthodontic lab technicians will typically fabricate a cast mass-type appliance exhibiting a section of hard, stainless steel wire, with its two ends embedded in the cast mass as shown in FIG. 1.

The mid-span of the resilient stainless steel wire is supported as the wire extends outward between teeth on either side of the patient's arch. The mid-span section of the wire spans the outer surfaces of the anterior teeth and is commonly referred to as a "labial bow". A typical cast mass-type appliance as described, containing embedded metallic devices that act on both the inside and outside surfaces (i.e. with a labial bow on the outside of the teeth) of some or all of the teeth constitutes one common and well-known type of orthodontic appliance.

As can be appreciated, the interaction of the loaded spring devices on the inside of the teeth may push the crowns outward until such time that they contact the labial bow. Over the course of treatment, the crowns may contact the labial bow but nonetheless still exhibit an undesirable rotation. It is the continued pushing of the springs on the teeth from the inside, against the labial bow, that will slowly rotate the tooth to a desirable corrected position.

To best contrast the advantages and benefits of the present invention, it is necessary to describe the well known limitations and shortcomings of current cast-mass-type appliances. First, it must be appreciated that the physiological response elicited from current cast mass-type appliances proceeds very slowly, consuming many months of treatment time. The second and most notable shortcoming of the current-design cast mass-type appliance that the present inventive system of springs favorably improves upon is that such appliances have no control whatsoever over the important consideration of alignment of the roots of the teeth. The movement of the teeth accomplished by current cast-mass-type appliances can be likened to uprighting a "stick stuck into sand", where the portion of the stick buried in the sand rotates around an unknown center of resistance with its lower extremities moving through the sand in one direction and its upper extremities moving in the opposite direction.

The absence of the ability to control the true location of an uprighted tooth is a major drawback and thus the use of cast mass-type appliances is limited. Nonetheless, cast mass-type appliances serve as useful adjuncts to other primary treatment methods (e.g., conventional braces) used to accomplish treatment goals during the active phase of orthodontic treatment.

To further illustrate the nature of the limitations of current cast mass-type appliances, it should be understood that the metallic devices embedded in cast mass-type appliances are capable of simple, single-vector correction of the inclination of the crowns of lingually-disposed teeth in an outward direction. The outer bow feature of such an appliance serves as a stop, limiting the correction to a roughly desired inclination. All of the limitations of such appliances described above are generally recognized by orthodontists and orthodontic laboratory technicians. In particular, such appliances are recognized, as being incapable of generating the more complex couple-type forces required to bodily move the roots of teeth through the supporting bone. The term "couple" is defined as the relationship between any two forces acting on a body where in combination, those forces tend to cause that body to rotate about a point. In contrast to a couple, the simple single-vector corrective forces generated by current cast mass-type appliances act only on the crown of a tooth and serve only to tip a tooth about its centroid.

The term "centroid" in the dental lexicon describes the theoretical center of resistance of a tooth's root as it is rotated through its alveolar bone structure in response to a single force applied, over time, to some point on its visible crown. The location of the center of resistance/center of rotation (i.e. the centroid) is hidden well below the gingival margin of a tooth at a theoretical point within the root. This biological centroid can again be thought of as being similar to the neutral rotation point as in the example above describing a stick being uprighted in sand.

Even though useful for some treatment objectives, orthodontists do not use such cast mass-type appliances as a primary corrective regimen. This is due to the inability of such appliances to bodily translate teeth through supportive bone as described. Such appliances are therefore typically relegated to serving as adjuncts to other primary labial methods (e.g., conventional "braces") as may be required for an individual patient's treatment.

A second type of orthodontic laboratory-produced appliance is also well known and is commercially fabricated in the same general manner and from generally the same group of materials as the appliance described above. This second type differs from the first in that rather than serving during the active tooth-moving phase of treatment, it serves to immobilize teeth in desirable positions, orientations and relationships after the active phase of treatment has ended. Such appliances are commonly referred to as "retainers" and differ from the first type of appliance described in that the metallic devices embedded in them are configured to hold teeth statically in their treated positions. Such appliances further serve to support or mechanically shelter the teeth against destabilizing forces or imbalances that may exist between the inwardly directed forces of the patient's facial musculature, the outward pressures of the tongue, as well as the deleterious effects of unanticipated post-treatment skeletal growth. This second type of appliance is successfully used for retention of the teeth because it's various shortcomings and limitations described above do not reduce its effectiveness in holding and retaining the teeth.

Retainers are typically prescribed for a patient by the dentist or orthodontist at the completion of regular orthodontic treatment. The attending orthodontist expects the retainer to maintain the results achieved during the active phase of treatment. The patient is instructed to begin wearing his or her retainer immediately after the braces are removed and to continue its use for a prescribed period of time thereafter. A patient then may remain in a post-treatment retention phase for one year or two years or even longer. In some cases, the attending orthodontist may prescribe that the post-treatment retention continues indefinitely. Indefinite (i.e. permanent) retention is indicated in particular cases where the patient's unique functional and physiological attributes clearly predispose the teeth for relapse.

Regarding orthodontic treatment generally, the orthodontic literature contains substantial references to the loss of the functional and aesthetic gains of orthodontic treatment after a period of time. See, Melrose et al., "Toward a Perspective on Orthodontic Retention?", *American Journal of Orthodontics and Dentofacial Orthopedics*, vol. 113, no. 5, pp. 507–514 (May 1998); Al Yami et al., "Stability of Orthodontic Treatment Outcome: Follow-Up Until 10 Years Postretention," *American Journal of Orthodontics and Dentofacial Orthopedics*, vol. 115, no. 3, pp. 300–304 (March 1999); Jarabak, *Technique and Treatment with Lightwire Edgewise Appliances*, vol. II, pp. 1143 et seq. (Mosby 1972); Graber, *Orthodontics Principles and Practice* (W. B. Saunders Company, 1972). Melrose et al. lament that there are no methods or reliable statistical means of determining a patient's propensity for post-treatment relapse, and no tools or reliable means to determine the correct minimum period of retention that will preclude relapse. The work by Al Yami et al. statistically paints a picture where perhaps only 67% of orthodontic cases can expect to remain stable for a 10-year post-treatment period. Graber even goes so far as to say that the fundamental step of attempting to retain teeth creates an artificial and unstable gnathologic condition and in the final analysis, it is necessitated by failure to achieve the primary orthodontic goals of treatment to a stable, functional occlusion.

Relapsed cases are also referred to as "failed cases" or "collapsed cases" and occur when individual teeth or groups of teeth move into undesirable positions and undesirable relationships. There are multiple causes for such collapsed cases outside of periodontal compromise, including loss of anchorage due to the teeth being precariously positioned relative to the underlying bone, the compressive effects of interference resulting from unanticipated post-treatment growth of the face and particularly the mandible, the continued presence of destructive swallowing or sucking habits, abnormally taut facial musculature, fundamental misjudgment on the part of the orthodontist in the planning of treatment, misdiagnosis of the nature of the original malocclusion and non-cooperation in a case where a patient fails to wear his or her retainer as prescribed or fails to follow other instructions of the orthodontist.

A typical collapsed case will typically begin with the loss of normal interproximal contacts of the lower anterior teeth, usually due to a gradual loss of proper torque of the of the upper anterior teeth leading to a general decrease in arch length. The resulting compressive forces act to compress and push the lower front teeth together. Lacking normal contact with adjacent teeth, sometimes combined with interference from opposing teeth, one tooth or another will rotate or tip out of alignment and then slip in front of, or behind an adjacent tooth. Once the combinative support and stability provided by normal gnathological interdigitation and normal interproximal contacts of the lower anterior teeth are lost, all of the lower anterior teeth may begin to tip or splay inward as a group. Likewise in the upper arch, ideal tooth positioning that may have been achieved and supported during the active phase of treatment may degrade once the orthodontic hardware is removed. The upper front teeth may tip as a group in response to an imbalance between the outward forces of the tongue and the inward forces of the facial musculature.

Such cases are very discouraging for a patient when the hard-won and aesthetically-pleasing results of treatment are lost. Collapsed cases are an all too common disappointment for the orthodontic patient who sees the expense and inconvenience of his or her treatment as culminating in failure. The present invention provides a new and important option to patients whose treatment has failed. The present invention serves well to restore the orthodontic gains achieved during the active phase of treatment. In the past, a patient's options were limited to simply accepting the failure of his or her treatment, or considering undergoing the process of orthodontic treatment for a second time.

3. Solution to the Problem

The present invention involves a novel system of spring devices that are fabricated from new materials that are activated and adapted to the teeth in new ways. The present invention is a system of springs capable of loading the alveolar bone which supports the roots of the teeth in ways that elicits a fundamentally different type and rate of physiological response, allowing teeth to move much more quickly, thus allowing orthodontic treatment to be accomplished much more quickly than with any current methodologies. In combination, these new features and capabilities overcome the various limitations of the standard cast mass-type of appliance as well as open up the cast mass-type appliance for new and important treatment roles. The present inventive system of springs in combination with the cast mass-type appliance enable improved treatment methodologies for practitioners. The current invention enables the venerable cast mass-type appliance to see expanded application. Its new applications are directed toward both the fundamental challenges faced by orthodontists during active treatment, as well as the problem of correcting failed cases.

To illustrate one of the advantages of the current invention, it must be appreciated that most conventional orthodontic appliances are considered to be "fixed" in that they are permanently attached to the teeth and remain in place in the mouth until removed by the orthodontist. As a group, cast mass-type appliances are considered to be "removable" appliances because the patient can routinely put them in and take them out. In most cases, treatment with removable appliances typically proceeds with the appliance being worn only during the evenings and during sleep. Special cases may require that such appliances be worn more, particularly in the early stages of treatment, but generally, a patient always has the option of removing them. This allows the patient to avoid the many inconveniences and socially self-conscious aspects of orthodontic treatment (e.g., the unwanted "metal mouth" look). Removable appliances provide many practical advantages compared to fixed appliances and such advantages benefit the patient, the orthodontist and his staff. As can be appreciated, a removable cast mass-type appliance incorporating improvements of the present invention and thereby rendering it capable of achieving the primary objectives of orthodontic treatment is a development with tremendous treatment-related and commercial impact. Even though many patients stoically tolerate the nuisance-aspects of their orthodontic treatment such as its negative impact on the ability to speak normally and self-image issues, as well as eating and oral hygiene problems, the latitude of being able to not wear orthodontic devices during work, school and special social settings is extremely desirable.

Considering the present invention and its capacity for use as a means to correct failed or collapsed cases, patients whose original orthodontic treatment has collapsed are inherently older, and they may be of an age where they have entered the work force and/or started a career. One demographic model includes image-conscious young professional people whose desire for orthodontic correction is countered by a reluctance to repeat their earlier treatment, which would likely consume two to three years and would involve the negative stigma of "adult braces." Individuals falling into such a group would very likely find the feature of "removability" as a very important consideration and thus they may be much more apt to consider repeating orthodontic treatment if given the option of a treatment modality that may progress only during the evenings and during sleep. Further, the removable cast mass-type appliance inherently discloses less orthodontic hardware on the visible front teeth. Compared to conventional braces, the labial bow and one or more springs of the present invention are much less unsightly.

For these many reasons, the present invention represents an important improvement in the current standard of orthodontic care. The present invention has significant commercial potential in that it represents a new treatment modality that addresses basic shortcomings of traditional braces-type orthodontic treatment, and it has attributes that accommodates important lifestyle considerations for young adults needing orthodontic correction.

SUMMARY OF THE INVENTION

This invention provides a method and apparatus for orthodontic treatment employing a cast mass-type appliance with a labial bow and combinations of labial and lingual springs to produce multiple coupled forces on all or selected teeth. The lingual spring has a stem embedded in the appliance and a plurality of pairs of activation loops at its active, tooth-contacting end, which extend laterally outward from the longitudinal axis of the stem. The labial spring has a pair of opposing lateral wings for attachment to a labial bow, and one or more rabbit ears extending selectively either occlusally or gingivally along the labial surface of the tooth. The orthodontist may selectively pre-activate the springs so that the lingual spring exerts a labially-directed force from the lingual side of a tooth and the labial spring exerts a lingually-directed force from the labial side of a tooth. In addition to such activations, both the springs positioned on the inside and positioned on the outside of the teeth are typically simultaneously further activated in complementary ways to correct undesirable tooth rotations. The system of springs of the present invention are thereby typically configured and activated to load or stress the underlying alveolar bone in ways that would not normally occur. The stresses produced by such coupled orthodontic forces on the crown of the tooth that are then translated into the supporting bone are different than any of the forces that the bone would normally encounter in its natural process of accommodation of changes in its functional loading. Therefore, those forces are forces that the tooth's periodontal membrane and the surrounding region of bone are not evolutionarily equipped to accommodate or mechanically resist.

The biological impact of the present inventive system of springs should also be considered. All living tissue, including the tissues of the human body perpetually strive to maintain a sort of structural homeostasis, in balance with both systemic self-generated mechanical forces and external mechanical forces that are constantly changing. In particular, the bony structures of the human body are constantly engaged in the process of adapting to changes in loading. It is well known that the bony structures of the human body also change in response to genetically triggered growth signals, and that bones grow to a genetically predetermined extent.

The process whereby bone adapts to maintain a dynamic balance with changing structural demands is a naturally occurring response. For example, humans subjected to prolonged zero gravity in space experience loss of bone mass, whereas individuals whose vocation involves excessive loading of certain bones see those bones change in shape and increase in mass in response to those increased loads.

When observing the human mandible as it relates to orthodontics, it can be seen that unlike most other human bones, the mandible, exhibits a remarkable capability to remodel. For example, the mandible accommodates the arrival of molars at age 6 and again at age 12 by significantly lengthening in the horizontal axis relative to the vertical. Its overall shape will adapt and accommodate and comply with the position and angle of the opposing maxilla as well as the skeletal structure of the face and so on as it strives to maintain a functional balance in harmony with surrounding living structure. During growth of the individual as well as after skeletal maturity, the mandible clearly responds to a wide variety of reformative forces acting upon it.

The alveolar bone supporting both the upper and lower dentition is a particularly adaptive structure that participates in the maintenance of a dynamically balanced occlusion. The occlusion is influenced by the geometry of the temporal mandibular joint and vice versa. Each root of each tooth is encapsulated within a protective, elastic periodontal membrane, which in turn is positioned within the supportive alveolar bone and even though a mechanically structural system, the position of each tooth should be understood as imminently malleable. Together, all of the teeth continually vie for balance with the opposing and the adjacent teeth as well as with the inwardly and outwardly directed forces of the adjacent soft tissues.

The dynamic balance between all of the oral structures and the skeletal realities of all of the bony structures below the floor of the cranium, and indeed the cranium itself must be appreciated as a non-rigid, constantly adapting and malleable natural living mechanical system.

To best understand the present invention, it is necessary to first appreciate the symphony of inter-accommodative mechanical forces endlessly operative in the living structure, striving to maintain functional balance, and more particularly that the teeth and the alveolar bone participate in this dynamic balancing. A distinction must be made however regarding the nature of the forces that drive this process. One quality that these forces share is that they can all be considered as natural forces; not because they occur in living tissue but because the are all relatively large, single-direction vectors of compression or tension or bending that trigonometrically occur by default between the geometry of the structural members (the bones, the muscles, cartilaginous and connective tissues) involved.

To further characterize these natural forces, teeth must accommodate the intrusive/compressive forces of occlusion and mastication. The mandible itself must withstand a rather intense bending moment as is required to shear and crush food. The powerfully constrictive musculature between the sides of the skull and the mandible load all of the adjacent bony structures in compression. The forces that must be accommodated by structures such as the skull, the mandible and the alveolar bone supporting the teeth are considered to be functional forces and importantly, all of these living structures are of course ideally designed through the process of evolution to accommodate these naturally occurring forces associated with growing and living.

The current array of orthodontic armamentarium in worldwide use today is based on mechanical force delivery models capable of imparting forces that are actually similar to the simple, naturally occurring single-vector forces described above. Generally, the current array of orthodontic armamentarium acts to achieve orthodontic correction by the application of single vector corrective forces to a tooth or groups of teeth in a lineal sequence. For example, as described herein, prior art cast mass-type of appliances attempt to push on the crown of a tooth to desirably tip that tooth. Other types of appliances currently used within orthodontics attempt correction by selectively exerting similar pushing, pulling or twisting forces on teeth to urge them into desirable positions and orientations.

As can be appreciated from the foregoing, the underlying alveolar bone reacts to the introduction of such simple, single vector corrective forces as if those forces are like the naturally occurring functional forces described above. This then elicits a physiological response and the alveolar bone will slowly accommodate those forces producing tooth movement. The bone is in a sense being "tricked" into responding to the forces introduced by the conventional orthodontist as if they were the same as the naturally occurring forces that are accommodated for living balance.

The present invention achieves a rate of orthodontic response (i.e. the desirable repositioning of the roots of individual teeth) through the alveolar process that is approximately five times faster than what is considered to be a normal rate of tooth movement achieved during conventional orthodontic treatment. The markedly faster rate of orthodontic correction observed in treatment using the present invention is completely devoid of the pathological and sometimes necrotic sequella that is traditionally thought to be associated with such exceedingly rapid tooth movement.

For example, in the early years of orthodontics, very high forces were used to move teeth and such forces and such excessive forces typically resulted in resorption (shortening or blunting) of the roots of the teeth being moved, and associated trauma to the periosteal tissues and the surrounding bone. In controlled clinical settings, the present inventive system of springs used in conjunction with the cast mass-type appliances achieves markedly faster rates of tooth movement without any of these problems, and without any discomfort to the patient.

A physiological analysis of the basis of such rapid response, in light of current understandings of bone growth and bone remodeling as well as metallurgical advances incorporated into the present invention follows below.

In contrast to current orthodontic armamentarium, the present inventive system of springs delivers a resultant root-moving force vector that is always a "vector composite" of at least three or more distinctly separate, but closely coupled force vectors. By locally loading the living alveolar bone with a complex array of closely coupled but distinctly non-coplanar force vectors, the bone is structurally loaded in ways that are clearly outside of the category of forces that it is naturally designed to accommodate. Even though the resulting vector-sum of forces generated by the present invention may be identical in direction and amplitude to a simple, single vector force as is generated by the current orthodontic armamentarium, the fact that the present invention achieves that resultant vector by combining at least 3 multiple vectors seems to elicit a new and profoundly different type of response in the underlying bone. It is felt that this is the key to such remarkably fast, yet safe and painless rates of physiological response from the bone.

To better illustrate the way that the alveolar bone responds to the present invention, consider that the orthodontic literature is replete with research describing a conventional model of tooth movement. It is well known that a process called the "osteoclast/osteoblast" mode of tooth movement is operative in response to conventional orthodontic forces. The "osteoclast/osteoblast" mode of tooth movement describes a process where the resorption of bone is thought to occur in the direction of tooth movement and the process of deposition of bone occurs, which is the filling-in of new bone behind a tooth as it moves in response to a gentle, continuous force. Such tooth movement involves the movement of the root as well as its periodontal membrane through the bone.

Studies show that orthodontic treatment using the present inventive system of springs achieves a somewhat different mode of root translation. It involves the translation of a living assembly that is thought to involve the root, the periodontal membrane and importantly, the region of alveolar bone locally adjacent to, and surrounding the root and the periodontal membrane This living assembly can be considered as moving together as one physiologic unit. The interface between the moving physiologic unit and the surrounding alveolar bone is thought to extend significantly further away from the root than the conventional osteoclast/osteoblast model of tooth movement. Orthodontic treatment using the present inventive system of springs can perhaps be thought of as moving one region of tooth-supporting alveolar bone through a larger region of stationary alveolar bone.

All living organisms are the product of billions of years of evolution and billions of years of structural accommodation of the dynamic loads experienced by individuals. Only by the skilled intervention of orthodontists can the living structures of the mandible and maxilla be loaded with such concentrated and complex loading patterns so as to trigger such a different type of physiological response.

As described above, even though the net vector resultant of the multi-coupled forces generated by the present invention may be in a logical direction for treatment, it nonetheless is composed of a minimum of three distinct non-coplanar vector forces. Loading and stressing the underlying bone in this unnatural way produces an extraordinary and generally unobserved rapidity to the physiological tooth-moving response.

To further optimize the coupled forces that are carried to the underlying alveolar bone through contact of the teeth with the present inventive system, the springs can be formed of a chromium-cobalt alloy. The present invention further benefits from the desirable properties of this alloy through certain metallurgical treatments resulting in the alloy exhibiting its maximum work-hardened and heat-treated hard condition. Even though this alloy is known to be useful in unrelated orthodontic applications when used in generally larger diameters, the present invention employs the alloy in its hardest condition and in small diameters. The unique properties that result through the use of the alloy and its conditioning, further combined with the novel physical configurations of the formed configurations combinatively produce a highly optimized gentle and continuous physiological force that is ideally calibrated to elicit maximum response in the alveolar bone when loaded in the complex, multiple vector manner produced by the present invention.

These and other advantages, features, and benefits of the present invention will be more readily understood in view of the following detailed descriptions and the drawings.

BRIEF DESCRIPTION OF THE DRAWINGS

The present invention can be more readily understood in conjunction with the accompanying drawings, in which:

FIG. 2(a) is a perspective view of the lingual spring 30.

FIG. 2(b) is a perspective view of a folded version of the lingual spring 30.

FIGS. 5(a) and 5(b) are side elevational view of a labial spring 40 attached to a labial bow 25 showing one type of varying activation of the labial spring.

FIG. 6 is a view looking gingivally at the dental arch showing a lingual spring 30 after activation for rotating a tooth.

DETAILED DESCRIPTION OF THE INVENTION

Figure 1:
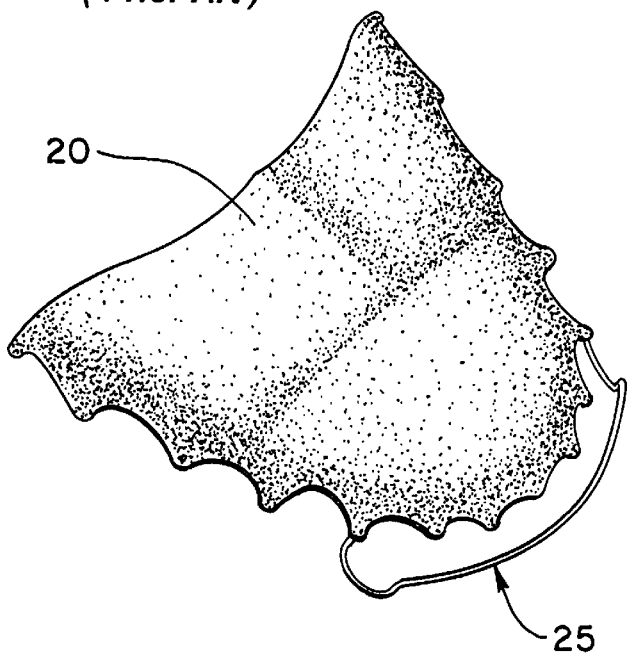
FIG. 1 is a perspective view of a prior art cast mass appliance with a labial bow.

The present invention consists of a combination of lingual and labial springs 30, 40 that when used in conjunction with a removable cast mass-type appliance 20 with an integral labial bow 25 are capable of fully controlling the position of the roots of the teeth, and are capable of eliciting a very rapid physiological response. The fundamental improvement over the prior art can be appreciated in the FIGS. 2(a) through 2(c). FIG. 3 depicts elements of the present invention configured in an orientation useful for rotating a tooth about a practitioner-determined point located within the visible crown of a tooth whereas prior art cast mass appliances were limited to tipping teeth about a non-practitioner-determined point (i.e. the resulting "centroid") which is located subgingival, and about ⅓ of the way down the root of a tooth. Both FIGS. 3 and 4 demonstrate the unique capabilities of the present invention where the point of rotation is located within the visible crown.

One combination of labial and lingual springs 30, 40 in accordance with the present invention are shown in the cross-sectional view provided in FIG. 3. The lingual spring 30 exerts a labially-directed force from the lingual side of a maxillary central tooth 10 and the labial spring 40 exerts a lingually-directed force from the labial side of a maxillary central tooth 10. Importantly, in addition to the two-force couple created by the interworking of the inner and outer springs 30 and 40, it must be appreciated that springs 30 and 40 can also simultaneously impart a desirable corrective rotational force to a tooth, thus imparting compressive, tensile and rotational vectors into the underlying bone.

FIGS. 2(a) is a perspective view of the lingual spring 30. FIG. 2(b) is a corresponding perspective view of a bent or folded version of the lingual spring 30. The stem 32 of the lingual spring 30 is embedded in the cast mass-type appliance 20 adjacent to a tooth that requires repositioning. The tooth-contacting portion of the lingual spring 30 comprises a plurality of pairs of activation loops 34 extending laterally outward from the longitudinal axis of the stem 32. In the preferred embodiment, the stem 32 and activation loops 34 are formed from a single continuous piece of wire. For example, the activation loops 34 can be permanently deformed by the orthodontist by bending, twisting, or stretching the wire locally beyond its elastic limit so that it is permanently reconfigured and set to exert a targeted force or combination of targeted forces about a desired rotation point while contacting the tooth at a desired location on its lingual surface.

Figure 2C:
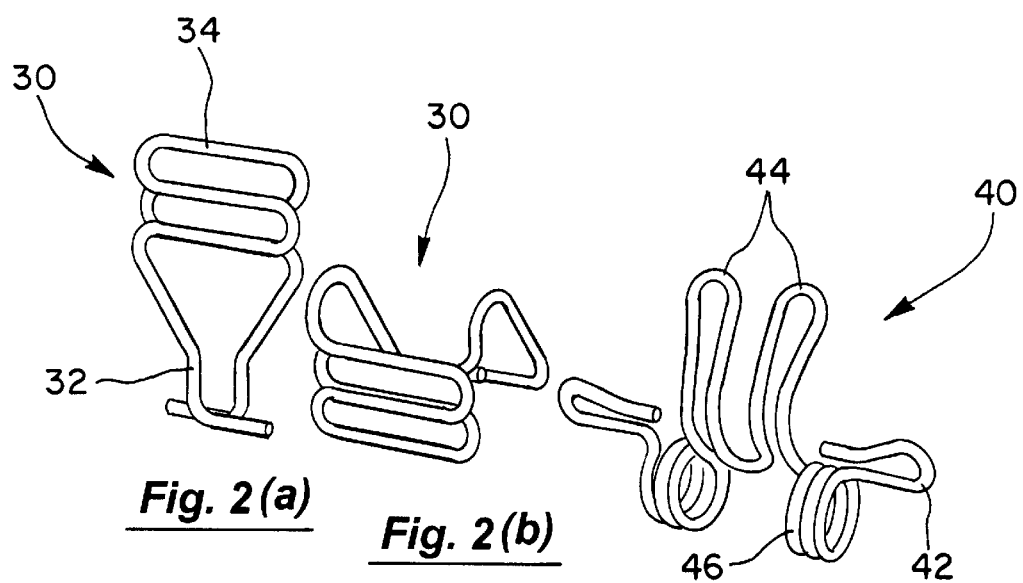
FIG. 2(c) is a perspective view of the labial spring 40.
Figure 3:
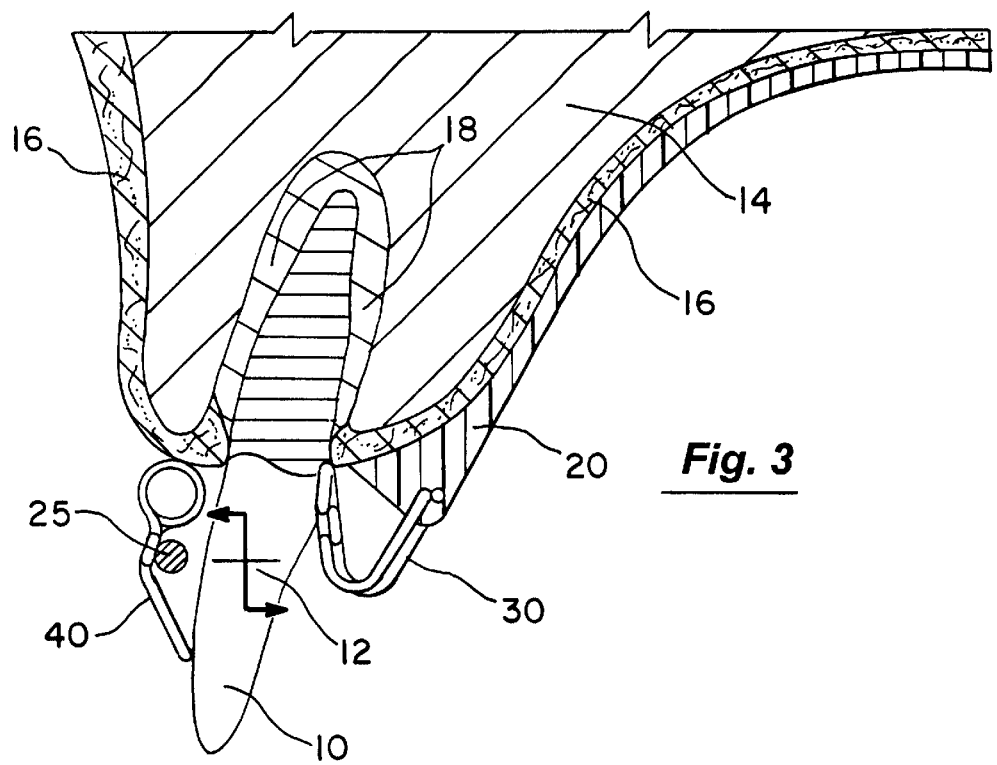
FIG. 3 is a cross-sectional view of a tooth 10, cast mass appliance 20, lingual spring 30, labial bow 25, and labial spring 40 which together cause the root of the tooth 10 to rotate about a predetermined point within the visible crown of a tooth in the labial (negative torque) direction.

FIG. 2(c) is a perspective view of a labial spring 40 designed to be tack-welded, then soldered to the labial bow 25 of the appliance 20. The labial spring 40 generally comprises a pair of lateral wings 42 for attachment to the labial bow 25, and one or more rabbit ears 44 extending generally normal to the axis of the labial bow 25. In the embodiment shown in the FIG. 2(c) the labial spring 40 has two rabbit ears 44 extending upward in substantially the same plane. Other cases may require that the labial spring be attached to the labial bow upside down so that the two rabbit ears extend instead generally downward. The rabbit ears 44 are typically permanently deformed by the orthodontist to exert a desired rotational force or rotational moment at a desired location on the labial side of a tooth 10. Typically in treatment, each of the rabbit ears are selectively over-activated or under-activated to achieve a desired differential rotational force in sympathetic accommodation of the lingual spring it co-works with.

As another method of achieving a differentially clockwise or counter clock-wise-biased rotational force, the labial springs 40 can also be provided with one or more helical spring sections 46 with more windings on one side or the other. Such a configuration produces an uneven but nonetheless wider, more constant orthodontic force, which is demonstrated to the tooth through the rabbit ears 44. In the preferred embodiment shown in FIG. 2(c), the labial spring 40 is formed from a single, continuous piece of wire.

As shown in FIG. 3, the stem 32 of the lingual spring 30 is embedded in a cast mass-type appliance 20 and its activation loops 34 contact the lingual side of the tooth 10 near the gingival margin, just above the lingual gum line. The labial spring 40 has been permanently and fixedly attached to the labial bow 25 of a cast mass-type appliance 20 and it has been activated so that its rabbit ears 44 contact the tooth 10 near the incisal edge of the tooth 10. This results in a trigonometric force vector being imparted to the tooth 10. For example, the labial spring (as mounted on the labial bow) and the lingual spring can exert forces on the tooth 10 to create a mechanical couple.

Pure couples are rarely seen operating alone in mechanical systems. Particularly in orthodontics, it must be appreciated that other forces, and even other couples may also be simultaneously acting on the so called point of rotation related to a tooth, causing that point to also be moving relative to the surrounding structure as it rotates. In response to forces generated by the present invention, a tooth may be desirably uprighted while it is being bodily repositioned while at the same time it is being desirably rotated.

To demonstrate the full action of the present invention, the forces described must be considered as existing simultaneously with the rotation-correcting forces also generated by selective activation of the present invention and that it is the coexisting nature of multiple couples and multiple force vectors that are one group of unique and innovative aspects of the present invention.

The multiple trigonometric couple that is created by the present inventive system differs in important ways from the simple axial rotational vector that causes a tooth 10 to rotate around a centroid located well down within the root. First, the capability of rotating a tooth into a corrected position about a center of rotation located inside the visible crown of the tooth rather than a point located well down within the root structure of a tooth is a typical objective of an orthodontist. Such improved control allows the orthodontist to direct the crown of the tooth desirably relative to the other teeth while also positioning the root securely, and desirably parallel to the adjacent roots for a stable and well-positioned inclination. Such bodily control is much more sophisticated than the type of control that prior-art cast mass appliances are capable of and therefore much more useful to the orthodontist.

FIG. 3 depicts a maxillary central tooth 10 positioned properly. Its inclination (i.e., torque value) is statistically correct at positive 11 degrees. It is desirably centered in the alveolar bone 18 (sometimes referred to as the tooth being centered "in the trough"). The alveolar bone 18 is the malleable, soft bone through which an orthodontist translates the roots of the teeth. The harder, denser cortical bone 14 holds the alveolar bone 18 in a trough of sorts. Soft tissue 16 covers the outer surface of the cortical bone 14.

Now, a typical orthodontic case presenting with mal-occluded maxillary central teeth may exhibit the maxillary central teeth with a desirable inclination yet the roots may be undesirably located against either the lingual or labial cortical bone. An orthodontist may refer to such root locations as being "not in the trough". In another case, the crown may be flared to either the labial or the lingual. A listing of the possible extremes where a mal-occluded maxillary central tooth may be found would include:

1. Crown flared labially and root locked labially against the cortical bone
2. Labially flared crown, and roots locked against the lingual cortical bone
3. Lingually canted crown and roots locked labially against the cortical bone
4. Lingually canted crown and roots locked lingually against the cortical bone.

As can be appreciated, traditional cast mass-type appliances can only correct an excessive labial or lingual cant of a tooth. The tooth may be uprighted to a proper inclination by such prior art appliances but such appliances have no capability to establish, control, or correct the resulting labio-lingual position of the crown within the alveolar bone once uprighted.

Since in the example recited above, the lingual spring 30 of the present inventive system exerts a labially-directed force at a point near the gingival margin while the labial spring 40 exerts a lingually-directed force near the incisal edge, two non-coplanar vectors combine to create a mechanical couple. The couple produces an axial vector that over time swings the root through the bone about a point 12 located within the visible crown. So, one advantage of the present invention is to provide a method for the orthodontist to both upright teeth and bodily move teeth so as to be desirably centered in the alveolar bone and in proper aesthetic and functional relation to the adjacent and opposing teeth.

Figure 4:
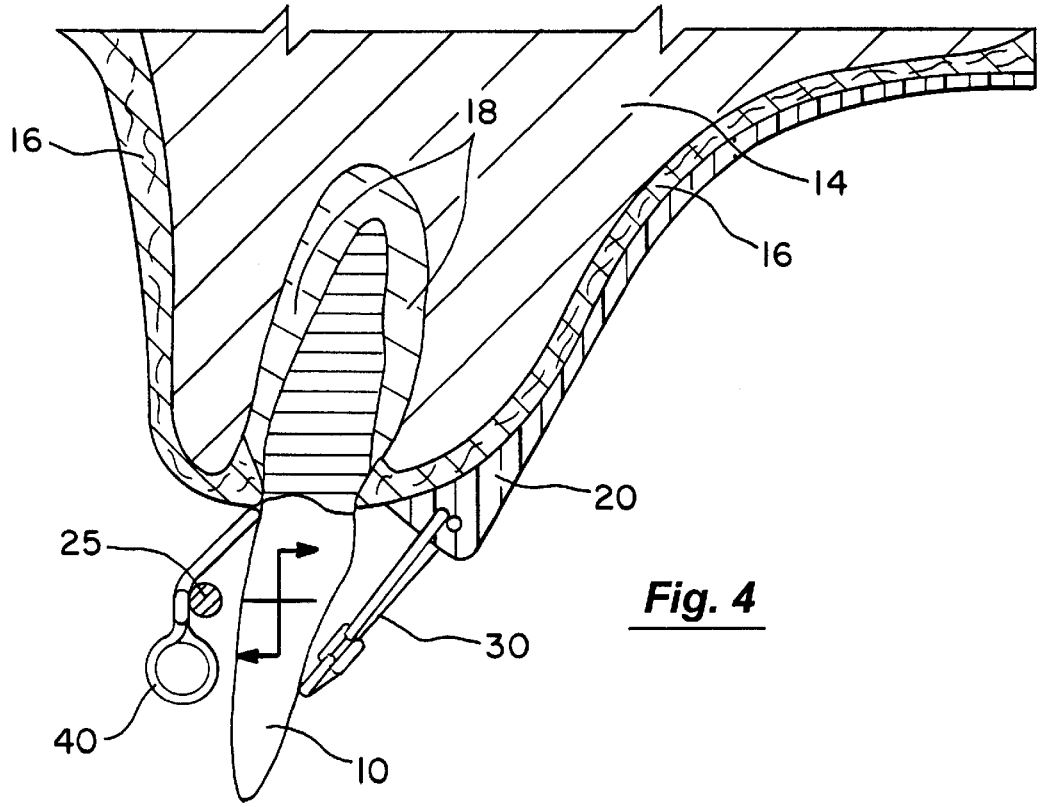
FIG. 4 is a cross-sectional view corresponding to FIG. 3 with the root of the tooth 10 being rotated about a predetermined point within the visible crown of a tooth in the lingual (positive torque) direction.

FIG. 4 depicts the cast mass appliance 20 and the present invention configured for rotating the root of the tooth 10 in a lingual (positive torque) direction. This configuration utilizes a lingual spring 30 (shown in FIG. 2(a)) in conjunction with a labial spring 40 (shown in FIG. 2(c)) positioned on the labial bow 25 but oriented upside down relative to the first example above.

The present system can also be employed to simultaneously correct undesirable rotations of teeth as the teeth are bodily moved and torqued into desirable positions and inclinations. "Rotation" is a term related to rotation of a tooth about its long axis, which in single-rooted teeth is an imaginary line extending through the tooth from the incisal edge of the crown to the apical tip of the root.

In addition to simultaneous activation for rotation, the relative degree of uprighting to be achieved versus the amount of bodily movement needed while both uprighting and repositioning a tooth can be differentially controlled by the practitioner through skillful activations to the present inventive system of springs. As described, activations for labio-lingual position and inclination are normally made in conjunction with activations intended to correct undesirable rotations To more clearly describe how an orthodontist can use these variable capabilities, a case may require: (1) correction in rotation; (2) significant bodily movement; and (3) relatively little uprighting; whereas another case may require moderate correction for rotation, significant uprighting but little bodily movement. A third case may present yet another hierarchy of correction objectives. The orthodontist can activate the current inventive system to accommodate this range.

The differential activation of the springs 30, 40 is accomplished as follows: First, the amount of energy that is stored in the labial spring 40 on the labial bow 25 is variable in several ways. For example, the labial spring 40 can be attached and soldered to the labial bow 25 in varying degrees of activation as shown in FIGS. 5(a) and 5(b). The aggressiveness of the correction for rotation can be set by selective activation of one or the other of the rabbit ears of the labial spring and a correspondingly opposite activation of the lingual spring to create a desired rotational couple.

Likewise, the activations, or more particularly the degree of activation can be skillfully controlled on the lingual side. In this way, both tipping/uprighting and bodily movements can be accomplished, but importantly, the dentist or orthodontist can differentially control the emphasis of the corrective forces as may be required by an individual's malocclusion. Correction of undesirable rotations in addition to uprighting are nearly always necessary since crowded and maloccluded teeth typically fall in front of or behind an adjacent tooth because some teeth must turn sideways to accommodate the compressive pressures of crowding. So, activation for inclination, activation for bodily repositioning and activations to correct undesirable rotations of the teeth are installed in the spring system comprising the present invention by the orthodontist at chairside.

When a cast mass appliance embodying such an array of activated springs provided by the present invention is installed in the mouth, malpositioned teeth, and the underlying alveolar bone can be subjected to a combination of three distinct, non-coplanar corrective vectors. Descriptions of the combinative capabilities of the springs 30, 40 to this point have addressed the ability of the present invention to control teeth in torque and the invention's capability to simultaneously reposition teeth bodily along with the invention's capability to simultaneously desirably rotate the teeth, all within the alveolar trough.

A typical pre-activation of the lingual spring 30 is shown in FIG. 6. The lingual spring 30 enables activation in two planes: (A) tilt and height adjustment in the vertical plane; and (B) rotation about the tooth's central axis. Due to the novel and innovative structure of the present invention, along with the novel use and condition of the wire alloy, along with its modified condition, the resultant force vector has a greater magnitude and range of action than conventional orthodontic springs.

Figure 7:
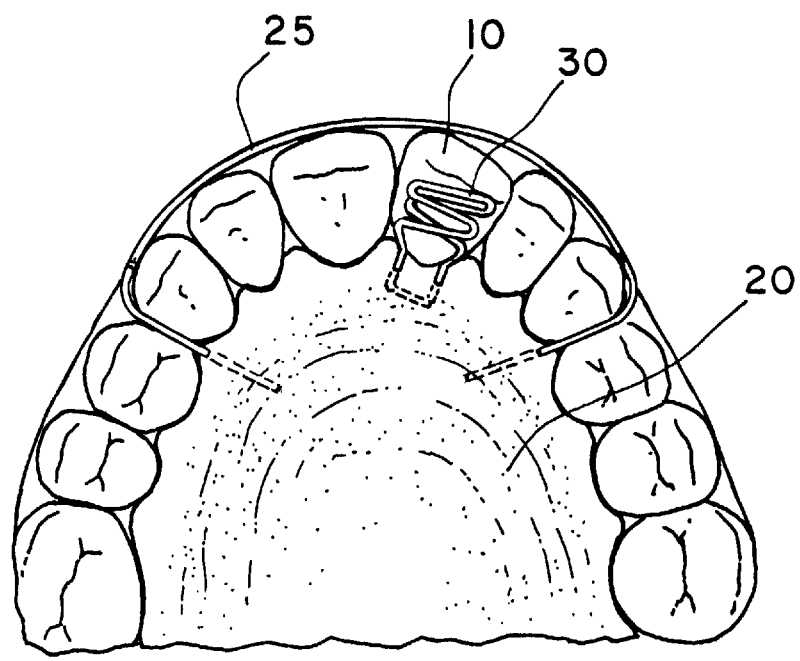
FIG. 7 is a diagram showing a lingual spring 30 after being activated to correct an undesirably rotated tooth and at the same time exert a desirable tipping force on the same tooth.

FIG. 7 shows an orthodontic appliance with a lingual spring 30 positioned in a typical activated configuration. The activated configuration is intended to impart among other forces, a force to correct an undesirable rotation of tooth 10. FIG. 7 shows an activation of approximately 30 to 45 degrees in the opposite direction of the rotated tooth. At insertion, the lingual spring 30 is tucked behind the rotated tooth 10 by the orthodontist or his or her staff. The resistant forces, retainer ball clasps and the point of contact of the labial bow 25 on the most labial point of the rotated tooth 10 keep the retainer from dislodging. As can be seen in FIG. 7, activation of the lingual spring 30 is aggressive and unconventional compared to activations typically installed in stainless steel orthodontic springs and appliances. Typically, orthodontic springs will be activated only to the degree that once the tooth has physiologically responded to the corrective force, the springs become passive. In other words, once the tooth is in its corrected position, conventional orthodontic springs "peter out". As can be appreciated from the above figure, the springs of the present inventive system will not "peter out", and in fact a tooth may pass from an initial undesirable position through a corrected position and continue on toward another undesirable position in the other direction without the intercedence of the orthodontist.

The present invention can be formed from an ultra-hard, chromium-cobalt alloy, designated as ASTM F1058 and known commercially as "Vectorloy", that is markedly different than conventional orthodontic wires and springs traditionally formed from stainless steel or the orthodontically-useful alloys of nickel-titanium, nickel-molybdenum, or nickel-copper-titanium. The nominal elemental constituents of the preferred chromium-cobalt alloy ASTM F1058 are: nickel 15.50%, cobalt 40.00%, chromium 20.00%, molybdenum 7.00%, manganese 2.00%, carbon 0.15%, with a balance of iron. Other alloys in the chromium-cobalt group are suitable for use in forming the present invention, including for example, ASTM F562, which is also known as MP35N. ASTM F562 alloy nominally contains the following elemental constituents: nickel 35.00%, cobalt 33.00%, chromium 20.00%, molybdenum 7.00%, iron 1.00%, silicone 0.15%, manganese 0.015%, carbon 0.025%, titanium 1.00%, phosphorous 0.015%, boron 0.010%, and sulfur 0.01%. In metallurgical terms, the essential active elemental constituent required to produce the mechanical properties required by the present invention in any alloy within the chromium-cobalt alloy group is cobalt. In order to obtain the mechanical properties suitable for the present invention, cobalt content of the alloy should be at least 30%.

The applicant's U.S. Pat. No. 5,984,675 describes the Vectorloy alloy in great detail and is incorporated herein by reference. The '675 patent describes the relationship between the unique mechanical properties of the present invention and a resulting optimal physiological response. The Vectorloy alloy is capable of being both work-hardened and then further hardened by heat-treating to a very high tensile strength that is beyond traditional dental wires. Small diameter wires (e.g., approximately 0.016 inch or 0.41 mm) of Vectorloy alloy provide an extremely appropriate and biologically effective force. The extremely low rate of the ultra-hard Vectorloy alloy, particularly when formed into the configurations of the present inventive system produces a near continuous, and therefore near ideal physiological force gradient. The combination of the physical spring design, including the use of a small diameter wire, further combined with the metallurgical and mechanical properties of Vectorloy result in an optimally bioengineered system of devices that produces heretofore unseen speed of orthodontic response.

Addressing the activations of the springs, this sequence is followed: Combinations of either or both of the two lingual versions of the springs 30 (shown in FIGS. 2(a) and 2(b)) are embedded in the cast mass appliance 20 by a laboratory technician as the appliance 20 is custom-fabricated according to the clinician's instructions to treat an individual patient's malocclusion. The various springs 30, 40 required for the patient's treatment are placed within the appliance 20 and attached to the labial bow 25 so that they passively contact the teeth when the appliance is placed in that patient's mouth. The attending orthodontist will then skillfully activate the springs 30, 40 using various standard dental pliers according to a pre-determined treatment plan for the subject patient. Activation of the system is confrontational. In other words, the springs are typically activated for rotation 30 degrees to 45 degrees in the opposite direction relative to the undesirable rotation of a tooth. This may be likened to a football player "putting his shoulder into it". The confrontational activation for rotation is best seen in FIG. 6. The 30° to 45° opposite activation has been determined to produce the best result.

Figure 8:
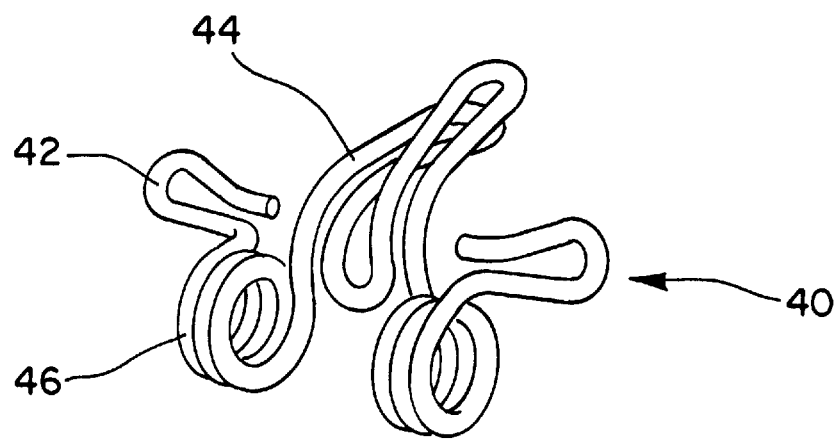
FIG. 8 is a front perspective view of a labial spring after being activated for rotation.

The labial spring 40 as described can similarly and cooperatively be biased against an undesirable rotation as shown in FIG. 8. As with activations for torque and bodily movement/position, activation for rotation can be differential. In other words, a mechanical couple is created as both lingual and labially directed forces are created in a vertical plane and a similar couple can be created in a horizontal plane. If the crown requires rotational correction as well as relocation to the lingual, the lingual force from the labial side will be emphasized, and the labial force from the lingual side will be correspondingly reduced. This combination will produce a rotation-correcting couple that produces rotational correction while emphasizing the lingually directed component, thus moving the tooth 10 lingually as the rotation is corrected. The foregoing is an example of the combinative ways that complementary activations can be made that accomplish multiple treatment goals simultaneously.

So, even though rotational control, torque control and bodily tooth movement have each been described separately above, in practice, a dentist or orthodontist will activate and appropriately bias the labial and lingual springs so as to accomplish the needed differential resultant corrective vector. That activation may combine torque, rotation and positional considerations into one skilled series of activations.

Since the present invention consists of both labial and lingual force-generators, and since the relative force each generates is controllable, and since those forces form rotational couples, the doctor can literally move teeth in virtually any resultant vector needed to accomplish a good, aesthetically-pleasing, stable finished result.

The unique capabilities and new treatment options afforded by the present invention enable the cast mass appliance to accomplish altogether new treatment functions. The cast mass appliance in accordance with the present invention can be used as the primary treatment modality since it is fully capable of virtually all types of tooth position correction, including correction of collapsed cases. Given the removable nature of cast mass appliances 20, such a primary correction appliance should gain popular acceptance with young adults who either never benefited from orthodontic treatment or experienced a relapse after treatment. Certainly such appliances are now capable of serving as an important option to conventional treatment methods using braces.

The above disclosure sets forth a number of embodiments of the present invention. Other arrangements or embodiments, not precisely set forth, could be practiced under the teachings of the present invention and as set forth in the following claims.

I claim:

1. An orthodontic appliance for correcting the position of selected teeth comprising:
    a removable appliance with a polymer substrate;
    a labial bow extending from the substrate of the appliance;
    at least one labial spring attached to the labial bow exerting a force on the labial surface of a tooth at a predetermined elevation; and
    at least one lingual spring having a stem embedded in the substrate of the removable appliance and a tooth-contacting end extending from the appliance to exert a force on the lingual surface of the tooth at a predetermined elevation; wherein the forces exerted by the labial spring and the lingual spring create a couple acting on a selected tooth.

2. The orthodontic appliance of claim 1 wherein the tooth-contacting end of the lingual spring further comprises a plurality of loops extending in series from the stem, with each loop having side portions extending laterally outward.

3. The orthodontic appliance of claim 1 wherein the lingual spring comprises a length of wire having ends forming the stem embedded in the substrate of the removable appliance and a plurality of loops extending in series from the stem forming the tooth-contacting end, wherein the loops can be deformed and extended to exert a force at a desired elevation and direction on the lingual surface of a tooth.

4. The orthodontic appliance of claim 1 wherein the lingual spring comprises a chromium-cobalt alloy.

5. The orthodontic appliance of claim 4 wherein the chromium-cobalt alloy comprises at least 30% cobalt.

6. The orthodontic appliance of claim 1 wherein the labial spring further comprises opposing lateral wings for attachment to the labial bow, and at least one rabbit ear extending to contact the labial surface of a tooth.

7. The orthodontic appliance of claim 6 wherein the labial spring further comprises a helical spring pressing the rabbit ear against the labial surface of the tooth.

8. The orthodontic appliance of claim 1 wherein the labial spring comprises a chromium-cobalt alloy.

9. The orthodontic appliance of claim 8 wherein the chromium-cobalt alloy comprises at least 30% cobalt.

10. An orthodontic appliance for correcting the position of selected teeth comprising:
    a removable appliance with a polymer substrate; and
    at least one lingual spring shaped from a length of wire having ends forming a stem embedded in the substrate of the removable appliance and opposing, generally S-shaped sides extending from the stem and toward a tooth that overlap one another to form a lineal series of loops, wherein the loops can be deformed and extended to exert a force at a desired elevation and direction on the lingual surface of a tooth.

11. The orthodontic appliance of claim 10 wherein the lingual spring comprises a chromium-cobalt alloy.

12. The orthodontic appliance of claim 11 wherein the chromium-cobalt alloy comprises at least 30% cobalt.

13. The orthodontic appliance of claim 10 further comprising a labial bow extending from the substrate of the appliance.

14. The orthodontic appliance of claim 13 further comprising a labial spring attached to the labial bow and exerting a force on the labial surface of a tooth, wherein the forces exerted by the labial spring and the lingual spring create a couple acting on a tooth.

15. The orthodontic appliance of claim 14 wherein the labial spring comprises a chromium-cobalt alloy.

16. The orthodontic appliance of claim 15 wherein the chromium-cobalt alloy comprises at least 30% cobalt.

17. The orthodontic appliance of claim 14 wherein the labial spring further comprises opposing lateral wings for attachment to the labial bow, and at least one rabbit ear extending to contact the labial surface of a tooth.

18. The orthodontic appliance of claim 13 wherein a force is exerted at a first elevation on the labial surface of a tooth via the labial bow, and the lingual spring exerts a force at a second elevation on the lingual surface of the tooth, thereby creating a couple acting on the tooth.

19. The orthodontic appliance of claim 10 wherein at least one loop of the lingual spring further comprises side portions extending laterally outward.

20. An orthodontic appliance for correcting the position of selected teeth comprising:
    a removable appliance with a polymer substrate;
    a labial bow extending from the substrate of the appliance;
    a labial spring having opposing lateral wings for attachment to the labial bow and at least one rabbit ear extending to contact and exert a force on the labial surface of a selected tooth at a predetermined elevation; and
    at least one lingual spring having a stem embedded in the substrate of the removable appliance and a tooth-contacting end extending from the appliance to exert a force on the lingual surface of the tooth at a predetermined elevation; wherein the forces exerted by the labial spring and the lingual spring create a couple acting on the tooth.

21. The orthodontic appliance of claim 20 wherein the labial spring further comprises a helical spring pressing the rabbit ear against the labial surface of the tooth.

22. The orthodontic appliance of claim 20 wherein the tooth-contacting end of the lingual spring further comprises a plurality of loops extending in series from the stem, wherein the loops can be deformed and extended to exert a force at a desired elevation and direction on the lingual surface of a tooth.

23. The orthodontic appliance of claim 22 wherein at least one loop of the lingual spring further comprises side portions extending laterally outward.

24. The orthodontic appliance of claim 20 wherein the lingual spring comprises a length of wire having ends forming the stem embedded in the substrate of the removable appliance and a plurality of loops extending in series from the stem.

25. The orthodontic appliance of claim 20 wherein the lingual spring comprises a chromium-cobalt alloy.

26. The orthodontic appliance of claim 25 wherein the chromium-cobalt alloy comprises at least 30% cobalt.

* * * * *